US011000068B2

(12) United States Patent
Marsot et al.

(10) Patent No.: US 11,000,068 B2
(45) Date of Patent: May 11, 2021

(54) AEROSOL INHALANT PRODUCING DEVICE WITH MEASURABLE DOSE AND/OR OTHER FEATURES

(71) Applicant: Cascadia Technologies, LLC, Portland, OR (US)

(72) Inventors: Travis Ryan Marsot, Mountain View, CA (US); Fritz Junker, Portland, OR (US)

(73) Assignee: CASCADIA TECHNOLOGIES, LLC, Portland, OR (US)

(*) Notice: Subject to any disclaimer, the term of this patent is extended or adjusted under 35 U.S.C. 154(b) by 355 days.

(21) Appl. No.: 16/012,159

(22) Filed: Jun. 19, 2018

(65) Prior Publication Data

US 2018/0360110 A1    Dec. 20, 2018

Related U.S. Application Data

(60) Provisional application No. 62/522,567, filed on Jun. 20, 2017.

(51) Int. Cl.
*A61M 16/12* (2006.01)
*A61M 16/20* (2006.01)
(Continued)

(52) U.S. Cl.
CPC ......... *A24F 47/002* (2013.01); *A61M 11/042* (2014.02); *A61M 15/0003* (2014.02);
(Continued)

(58) Field of Classification Search
CPC ....... A24F 40/51; A24F 47/008; A61J 1/2037; A61J 1/2089; A61K 9/1647; A61M 11/042; A61M 15/0003; A61M 15/002; A61M 15/0043; A61M 15/0045; A61M 15/0051; A61M 15/0055; A61M 15/0071; A61M 15/0076; A61M 15/008; A61M 15/0081; A61M 15/0083; A61M 15/009; A61M 15/06; A61M 15/08; A61M 2016/0021;
(Continued)

(56) References Cited

U.S. PATENT DOCUMENTS 4,300,546 A    11/1981   Kruber
5,326,228 A *   7/1994   Armitage ................ B05B 7/262
                                                                 417/151
(Continued)

FOREIGN PATENT DOCUMENTS

KR    20100032662    3/2010
WO    WO 2013040193    3/2013
WO    WO 2016012102    1/2016

OTHER PUBLICATIONS

U.S. Appl. No. 62/522,567, filed Jun. 20, 2017, Marsot.
(Continued)

*Primary Examiner* — Annette Dixon
(74) *Attorney, Agent, or Firm* — Ray Quinney & Nebeker P.C.; Paul N. Taylor

(57) ABSTRACT

A vaporizer device may include a plurality of cartridges with a plurality of aerosolization assemblies. The plurality of cartridges may include a suspension media and an additive media. The plurality of aerosolization assemblies may include pressurized cartridges connected to a nozzle having a nozzle opening of less than 20 micrometers.

20 Claims, 13 Drawing Sheets

(51) Int. Cl.
*A61M 15/00* (2006.01)
*A24F 47/00* (2020.01)
*A61M 11/04* (2006.01)
*A61M 11/02* (2006.01)

(52) U.S. Cl.
CPC ...... *A61M 15/009* (2013.01); *A61M 15/0013* (2014.02); *A61M 11/02* (2013.01); *A61M 16/208* (2013.01); *A61M 2205/3653* (2013.01); *A61M 2205/8206* (2013.01); *A61M 2205/8237* (2013.01)

(58) Field of Classification Search
CPC .. A61M 2016/0027; A61M 2202/0225; A61M 2205/3331; A61M 2205/3355; A61M 2205/3653; A61M 2205/8206; A61M 2205/8225; A61M 25/0097; A61M 5/007; A61M 5/1408; A61M 5/16854; A61P 11/00; A61P 11/06; A61P 11/08; A61P 25/00; A61P 25/04; A61P 31/04; A61P 37/08; A61P 43/00; B01F 3/0407; B05B 7/262; B65D 83/207; B65D 83/285; B65D 83/54; B65D 83/682; B65D 83/756; H05B 2203/003; H05B 3/265

See application file for complete search history.

(56) References Cited

U.S. PATENT DOCUMENTS

| | | | |
|---|---|---|---|
| 5,470,311 A * | 11/1995 | Setterstrom | A61K 9/1647 128/200.14 |
| 8,881,737 B2 * | 11/2014 | Collett | H05B 3/265 131/273 |
| 9,545,487 B2 | 1/2017 | Besseler et al. | |
| 2002/0092520 A1 | 7/2002 | Casper et al. | |
| 2003/0127538 A1 | 7/2003 | Patel et al. | |
| 2004/0031485 A1 | 2/2004 | Rustad et al. | |
| 2005/0247312 A1 * | 11/2005 | Davies | A61P 11/06 128/203.15 |
| 2006/0149214 A1 * | 7/2006 | Breiter | A61M 5/007 604/500 |
| 2007/0154407 A1 | 7/2007 | Peters et al. | |
| 2008/0184993 A1 | 8/2008 | Patel et al. | |
| 2010/0269818 A1 | 10/2010 | Abrams | |
| 2011/0277760 A1 | 11/2011 | Terry et al. | |
| 2012/0055467 A1 * | 3/2012 | Brambilla | B65D 83/682 128/200.21 |
| 2012/0059311 A1 * | 3/2012 | Gilbert | A61M 15/08 604/26 |
| 2013/0206142 A1 | 8/2013 | Dudley et al. | |
| 2015/0320116 A1 | 11/2015 | Bleloch et al. | |
| 2015/0328415 A1 | 11/2015 | Minskoff et al. | |
| 2016/0262454 A1 * | 9/2016 | Sears | A61M 11/042 |
| 2017/0027225 A1 * | 2/2017 | Buchberger | A61M 11/042 |

OTHER PUBLICATIONS

Ibrahim, M. et al, "Inhalation Drug Delivery Devices: Technology Update", *Medical Devices: Evidence and Research*; 8: Feb. 12, 2015; pp. 131-139.

Kwok, P.C.L., et al., "E-Cigarettes: Learnings for inhalation scientists", *Inhalation* Magazine, Dec. 2016, pp. 20-25.

* cited by examiner

AEROSOL INHALANT PRODUCING DEVICE WITH MEASURABLE DOSE AND/OR OTHER FEATURES

CROSS REFERENCE TO RELATED APPLICATIONS

This application claims the benefit of and priority to U.S. Provisional Patent Application Ser. No. 62/522,567, filed Jun. 20, 2017, which is hereby incorporated by reference in its entirety.

FIELD OF THE INVENTION

The present invention relates to devices that produce a vapor or aerosol for inhalation. These devices may include, but are not limited to, e-cigarettes, vaporizers, atomizers and like devices. More specifically, the present invention relates to an enabling technology that adds and integrates with previous devices. This includes, but is not limited to, nebulizing an inhalant to improve absorption into the mucosa of the lungs, providing measurable and/or multiple dosing additive delivery, providing replaceable additive cartridge options, and automating the vaporization and/or additive nebulizing process, among other aspects.

BACKGROUND

Devices that produce an aerosol for inhalation include electronic cigarettes and conventional pharmaceutical inhalers, among other devices. Electronic cigarettes are less regulated and relatively inexpensive, while conventional pharmaceutical inhalers are subject to FDA (U.S. Food and Drug Administration) regulation and may be significantly more expensive. Both represent a method of producing an aerosol for inhalation. Electronic cigarettes often use thermal vaporization to form the aerosol.

Vaporizers typically produce aerosol through heating a small volume of solution known as an e-liquid. The e-liquid often includes (1) nicotine, as e-cigarettes may be used as a smoking alternative or in smoking cessation, and (2) a carrier such as vegetable glycerin, propylene glycol and/or other substances. They may also include flavoring or other substance. Vaporizers are sometimes referred to as "e-cigarettes." The droplets suspended in the vapor are small, less than a micrometer, and hence allow inhalation deep into the lungs. A more general term for this conversion from liquid to vapor is aerosolization.

There are three classes of vaporizers. E-cigarettes, or EC's, are tubular in appearance and may resemble a tobacco cigarette or cigar. They have either rechargeable or non-rechargeable batteries, and are frequently disposable. Advanced vaporizers, sometimes called cartomizers, are built with more durable materials and feature modular construction that includes heater cartridges or refillable reservoirs. Cartomizers generally have higher power capabilities, and are larger with larger batteries and reservoirs. Specialty vaporizers may be called tanks or mods (modifiable). They have higher capacity batteries and a wider range of electronic controls. The heater assembly with these specialty vaporizers is often built by hand by a hobbyist. A primer on the current state of vaporizers and related inhalation science is provided in the article "E-cigarettes: Learnings for Inhalation Scientists," by Philip Chi Lip Kwok, et al., in the December 2016 issue of Inhalation magazine. This article is hereby incorporated by reference.

The Voke inhaler (non-thermal activation) and the e-Voke electronic inhaler (thermal activation) from Kind Consumer, London, England, have received regulatory approval in Great Britain for use in tobacco smoking cessation.

Furthermore, in the United States, in states where marijuana is legal, vaporizers have been configured for cannabinoid. These devices may use combustion or vaporization. These devices generally vaporize an oil-based media.

One way to create an aerosol is to pressurize the liquid form of the inhalant and force it through a relatively small opening. The rapid loss of pressure at the outlet generates a fine mist. This process may be referred to as "nebulization" and a device that performs it is a "nebulizer." A common example of a nebulizer is a nasal spray bottle. Asthma inhalers also nebulize, typically with a compressed gas or "propellant."

BRIEF SUMMARY

In some embodiments, an inhalant media in a plurality of cartridges may be aerosolized using a aerosolization assembly. The inhalant media may include a suspension media and an additive media. The nebulizing assembly may measure a measured dose. The nebulizing assembly may be actuated by an actuator.

In other embodiments, a plurality of inhalant media reservoirs including inhalant media may be nebulized using a nebulizing assembly. The nebulizing assembly may be controlled by an electronic control circuit according to input from a user.

This summary is provided to introduce a selection of concepts that are further described below in the detailed description. This summary is not intended to identify key or essential features of the claimed subject matter, nor is it intended to be used as an aid in limiting the scope of the claimed subject matter.

The attainment of the foregoing and related advantages and features of the invention should be more readily apparent to those skilled in the art, after review of the following more detailed description of the invention taken together with the drawings.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
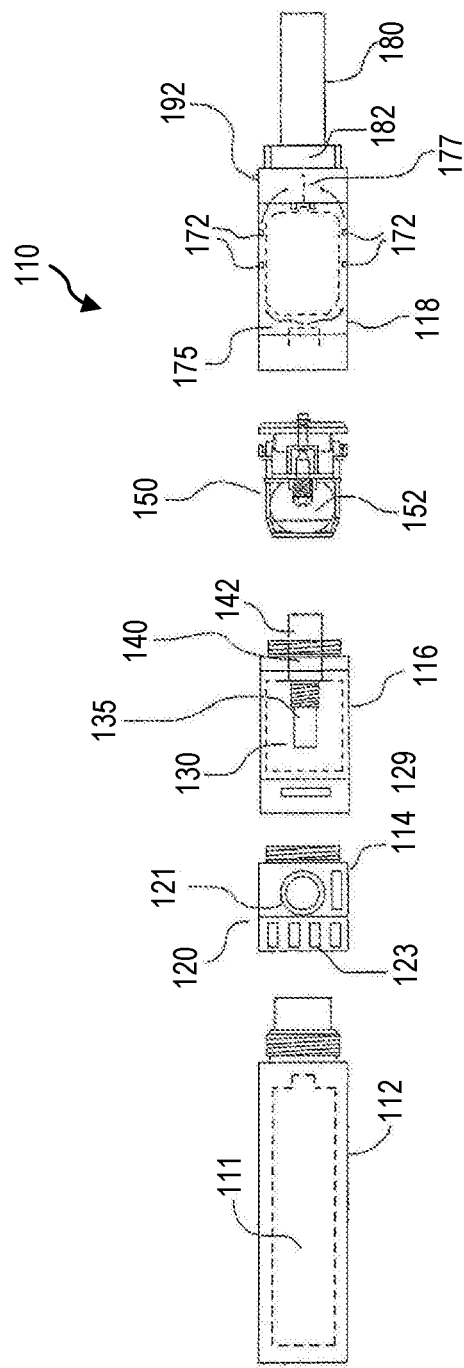
FIG. 1 is an exploded view of a vaporizer device, according to at least one embodiment of the present disclosure.

Referring to FIG. 1, an exploded view of one embodiment of a vaporizer device 110 is shown. Vaporizer device 110 may include a plurality of interconnecting housing sections (e.g., housing sections 112, 114, 116, 118) that house various components.

Battery housing section 112 may be configured to hold a battery 111 and couple releasably to control module 120. Control module 120, contained within housing section 114, may include an on-off button 121 and a user display or interface 123. This display/interface may include lights or a screen or other indicators for various parameters including, but not limited to, battery status, inhalant media level, inhalation chamber temperature or readiness for inhalation, dose setting, doses left, and/or other information.

In some embodiments, control module 120 may be coupled to first inhalant media reservoir 130 and thermal excitation assembly, including heating element 140 and wick 135 which may both be located within the housing section 116. Wick 135 may transport the first inhalant media into proximity with heating element 140 for aerosolization. The aerosolized first inhalant media may then pass through the first inhalant media outlet 142 for inhalation, ultimately, at mouthpiece 180. In some embodiments, an inlet air hole 129 may have an adjustable opening size. Suction on the mouthpiece 180 may create an airflow through the inlet air hole 129 to carry the aerosolized first inhalant media.

A nebulizer assembly 150 may be housed in housing section 118. Housing section 118 may be releasably coupled to housing section 116 to permit the ready replacement of a nebulizer assembly once the second inhalant reservoir is spent. In the exploded view of FIG. 1, the nebulizer assembly ("NA") is shown in solid lines outside of housing section 118 (for clarity of view) and in phantom line within the housing section (to show a representative position). First inhalant media outlet 142 is also provided in phantom lines (to shown position).

In some embodiments, tabs or protrusions 172 may properly seat nebulizer assembly (NA) 150 within housing section 118. The exterior cylindrical walls of NA 150 may be configured to form airflow channels or an airflow pathway around NA 150 for movement of the aerosolized first inhalant media 175 towards mouthpiece 180. For example, protrusions 172 may seat NA 150 to ensure adequate clearance for the first inhalant media 175 to pass through the housing section 118. Protrusions 172 may locate the nebulizer output port so that the aerosolized first media and second media mix before inhalation.

In some embodiments, NA 150 may include a second inhalant media reservoir 152 from which a second inhalant media may be aerosolized and mixed with the aerosolized first inhalant media 175. The aerosolized first inhalant media 175 may mix with the aerosolized second inhalant media 177 in output chamber 182. In some embodiments, output chamber 182 has a contoured interior surface. The mixed aerosolized first inhalant media 175 and aerosolized second inhalant media 177 may then be inhaled through mouthpiece 180.

In some embodiments, the first inhalant media may be suspension media. In other embodiments, the first and second inhalant media may be additive media. In still other embodiments, the first and second inhalant media may be different. For example, the first inhalant media may be a suspension media, and the second inhalant media may be an additive media. In other examples, the first inhalant media may be an additive media, and the second inhalant media may be a suspension media.

In some embodiments, the vaporizer device 110 may include an actuator 192 for triggering an aerosolization event or cycle. For example, the actuator 192 may be a mechanical actuator 192, including a spring biased pin or the like with a locked position that a user must engage for activation, thereby preventing accidental discharge. Indicator lights at display or interface 123 could indicate a ready state prior to discharge. In other examples, actuator 192 could be an electronic actuator 192, and may electronically lock (through a relay or the like) activation until other conditions are met. In some examples, those conditions may include temperature of heating element (i.e., readiness for suspension media vaporization), presence of inhalant media, etc. In some examples, those conditions may include instructions from a user. In other examples, the conditions may include instructions by the control module 120 to unlock the aerosolization assembly.

In some embodiments, the plurality of aerosolization assemblies may be locked to prevent accidental discharge. In some embodiments, the control module 120 may be configured to unlock at least one of the aerosolization assemblies according to instructions from a user.

Figure 2:
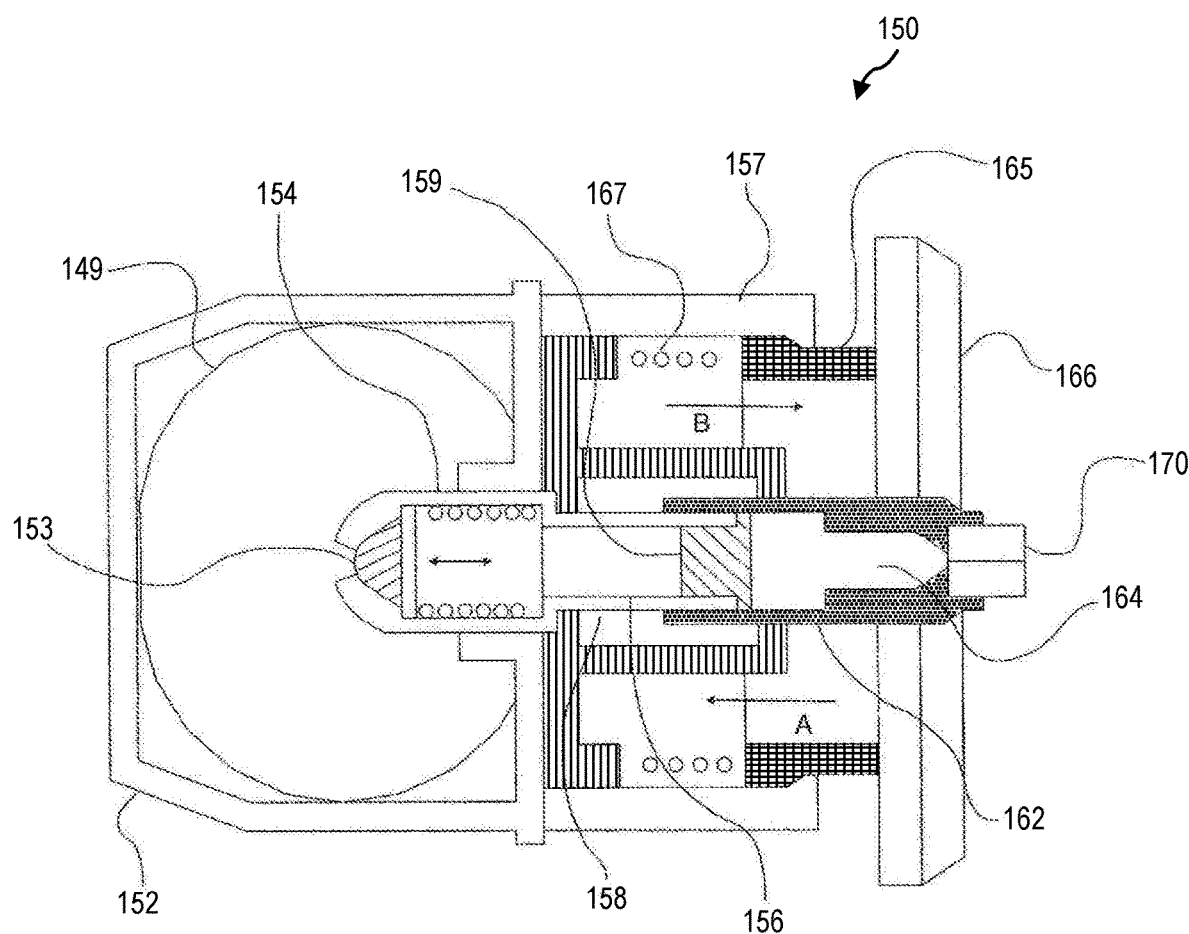
FIG. 2 is representation of a nebulizing assembly, according to at least one embodiment of the present disclosure.

Referring to FIG. 2, a longitudinal cross-sectional view of at least one embodiment of NA 150 is shown. In some embodiments, NA 150 may draw a measured or known amount of an inhalant media from inhalant media reservoir 152 and aerosolize it at nebulizer port 170.

In some embodiments, NA 150 may include an inhalant media reservoir 152 having a compressible liner 149 and an output at check valve 153. Check valve 153 may be biased towards a closed position by spring 154. Downstream of check valve 153 may be priming chamber 156. Priming chamber 156 may have an inner cylindrical wall 158 that telescopes within outer cylindrical wall 162. A non-return valve 159 may achieve one-way fluid flow between priming chamber 156 and piston chamber 164 as the outer cylindrical wall 162 telescopes over the inner cylindrical wall 158. The outer cylindrical wall 162 and the annular wall 165 may be coupled to cap 166. The annular wall 165 may be nested within additive side outer wall 157 and may be configured for telescoping movement. Spring 167 may bias the cap and piston in an extended or non-compressed position.

In some embodiments, NA 150 may be acted upon so that the cap and piston move in a first direction A (i.e., outer cylindrical wall 162 moving over inner cylindrical wall 158). The first direction A may compress the piston chamber 164 and force inhalant media within the piston chamber 164 through nebulizer port 170, thereby nebulizing the inhalant media and creating a puff of mist or aerosol at nebulizer port 170. When the compressing force is released, spring 167 may extend to the non-compressed position, extending the cap 166 to an extended position, and expanding piston chamber 164. Expanding piston chamber 164 may pull inhalant media from the priming chamber 156 into the piston chamber 164. Pulling inhalant media from the priming chamber 156 may pull inhalant media from the inhalant reservoir 152, past check valve 153 and against the bias of spring 154, into the priming chamber 156. The piston chamber 164 may then be recharged and ready for the next nebulization cycle. In some embodiments, the check valves and non-return valves may include any check valve or non-return valve. For example, the check valve or non-return valve may include a ball valve. In other examples, the check valve or non-return valve may include a butterfly valve. In still other examples, the check valve or non-return valve may include a diaphragm check valve.

In some embodiments, the mist or aerosol formed at nebulizer port 170 may then combine with the aerosolized first inhalant media 175 flowing past nebulizer port 170 and may be inhaled by a user at mouthpiece 180. The aerosolized first inhalant media 175 may continue to flow after the nebulizer assembly has been cycled to facilitate complete (or as nearly complete as practically possible) inhalation of the second inhalant media. For example, if the nebulizer assembly completes its cycle after the aerosolized first inhalant media 175 passes by the nebulizer port 170, a portion of the aerosolized second inhalant media may be entrained in the vaporizer device.

In some embodiments, NA 150 may come from the manufacturer with the priming and piston chambers already charged or filled, so that the first piston depression cycle results in an aerosolized second inhalant media at nebulizer port 170. In other embodiments, if the cartridge or chambers do not come pre-primed then priming activity may be required to load the chambers.

Referring to FIGS. 3A-3B, diagrams of electro-mechanical activation of NA 250 are shown. In some embodiments, cam-style actuator wheels 294 may be provided adjacent the cap 266 of NA 250. Upon actuation, the cams may be rotated to push the cap and piston downward/leftward, causing an evacuation of the piston chamber 164 through the nebulizer port 270. An electronic control circuit may be electrically coupled to the actuator cams and to various sensors, such as those measuring the parameters discussed above for a ready state. A user may respond to a ready indication by pushing the activation button for a discharge event. The electronic control circuit may then actuate actuator wheels 294. FIG. 3A illustrates the actuator wheels at rest (default) and FIG. 3B illustrates the actuator wheels at mid-stroke. Other examples of an actuator include electronic solenoid or voice coils.

FIG. 4 represents an exploded cross-sectional view of a vaporizer device 310, according to at least one embodiment of the present disclosure. Vaporizer device 310 may include a battery housing 312, control module 320, nebulizer assembly 350, output chamber 382 and mouthpiece 380.

In vaporizer device 310, the first inhalant media reservoir 330 may be configured to be releasably decouplable from the control module 320 and the wick 335 and heating element 340. Leftward arrows indicate reinsertion of the wick 335 and heating element 340 into the inhalant media reservoir and rightward arrows indicate the insertion of NA 350 into housing section 318 as discussed in relation to FIG. 1. This arrangement minimizes waste, and may be particularly suited for use when the same inhalant media is to be used. Rinsing of the wick may be desired if a different inhalant media is to be used (to avoid contamination) and/or to reduce the potential for clogging with repeated use.

Referring to FIG. 5, an exploded cross-sectional view of a vaporizer device 410 according to at least one embodiment of the present disclosure is shown. Vaporizer device 410 may operate in a manner similar to the other devices described herein and may include a battery housing 412, control module 420, a first inhalant media reservoir 430, a second inhalant reservoir 451, an output chamber 482, and a mouthpiece 480.

In vaporizer device 410, the first inhalant media reservoir 430 and second inhalant media reservoir 451 are configured with replaceable or interchangeable cartridges 431, 433. Each cartridge may additionally include a wick 435, a heating element 440 and one or more air passage channels 437. Air passage channel 437 of cartridge 433 may pass the aerosolized suspension media to the output of the additive reservoir cartridge 433. The two cartridge outputs may mix in output chamber 482 and be inhaled at mouthpiece 480.

The interchangeability of cartridges 431 and 433 permits a user to mix and match the inhalation products of their choice. In some embodiments, more than two cartridges may be used in series. For example, three, four, five, or six cartridges may be stacked in series. In other embodiments, multiple cartridges arranged in parallel may be used. In some embodiments, each cartridge may include a thermal excitation assembly. In other embodiments, each cartridge may include a nebulizing assembly. In still other embodiments, at least one cartridge may include a nebulizing assembly, and at least one cartridge may include a thermal excitation assembly. The parallel multiple units could be inserted into a singular housing section. For example, two cartridges may be inserted into a single housing section. In other examples, three cartridges may be inserted into a single housing section. In still other examples, two, three, four, five, or six cartridges may be arranged in a single housing section.

In some embodiments, dispensing of the first inhalant media may precede and follow the second inhalant media dispensing. In some embodiments, this may ensure all or most of the aerosolized second inhalant media is inhaled by the user. In some embodiments, this may achieve delivery of a more accurate dose by preparing the lungs and permitting inhalant penetration further into the lungs.

Figure 6:
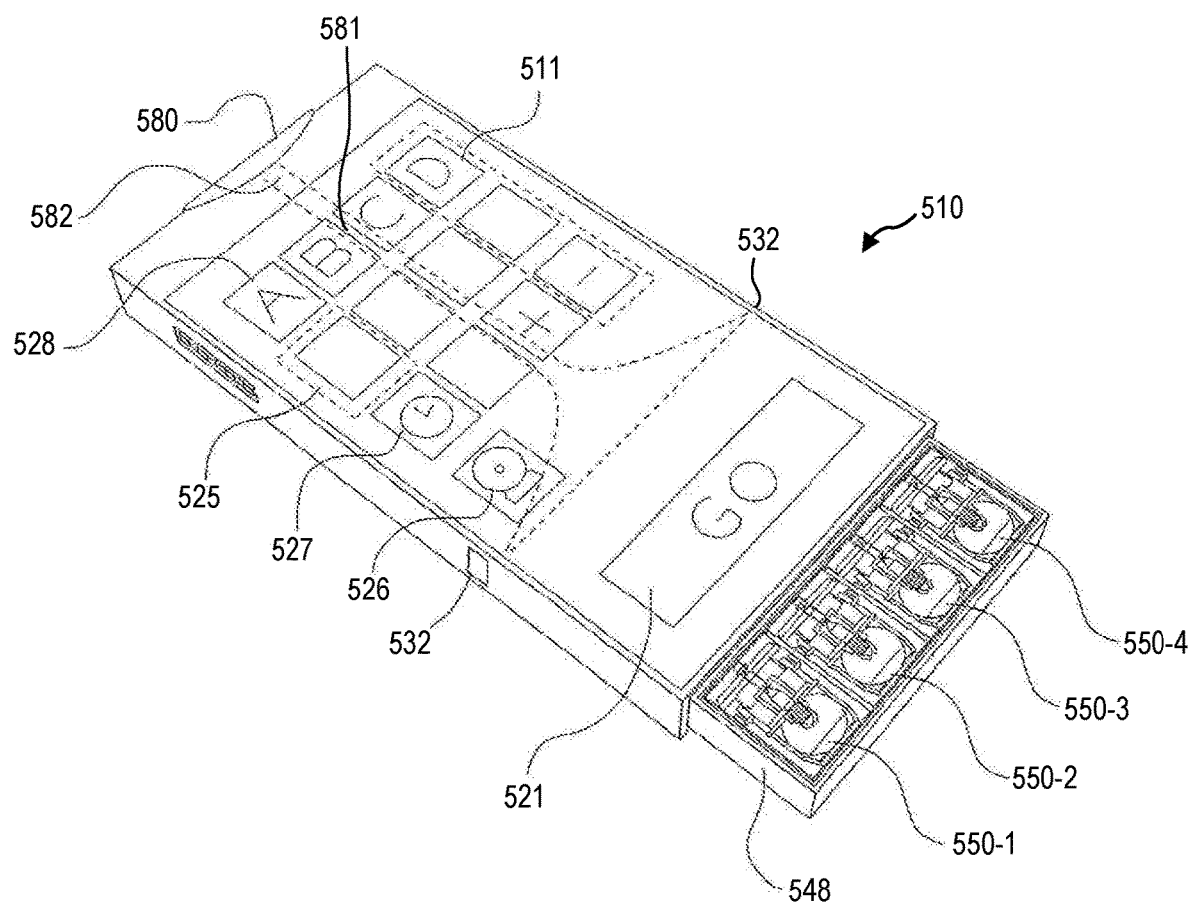
FIG. 6 is a vaporizer device according to at least one embodiment of the present disclosure.

Referring to FIG. 6, a perspective view of a vaporizer device 510 in accordance with at least one embodiment of the present disclosure is shown. In some embodiments, vaporizer device 510 may be configured as a pack including a battery 511, electronic control circuit 525, inhalant media cartridges 550-1, 550-2, 550-3, 550-4, output chamber 582 and mouthpiece 580.

Vaporizer Device 510 may also include a touch screen 528 having an on-off button 521, an alarm 526, a timer 527 and a keypad. Air holes 532 may connect to output chamber 582 which in turn may be coupled via conduit 581 to mouthpiece 580. Slide out drawer 548 may hold a plurality of inhalant media cartridges 550-1, 550-2, 550-3, 550-4. Each inhalant media cartridge 550-1, 550-2, 550-3, 550-4 may include an aerosolization assembly. In some embodiments, the inhalant media cartridges 550-1, 550-2, 550-3, 550-4 may include thermal excitation assemblies. In other embodiments, the inhalant media cartridges 550-1, 550-2, 550-3, 550-4 may include nebulizer assemblies. In still other embodiments, the inhalant media cartridges 550-1, 550-2, 550-3, 550-4 may include both thermal excitation assemblies and nebulizer assemblies.

Inhalant media cartridges 550-1, 550-2, 550-3, 550-4 may be configured in a manner that is the same or similar to that described above for NA 150 of FIG. 2 or, as shown below, FIGS. 11, 12, and 13. With drawer 548 inserted, the NAs may be arranged such that their output ports may be adjacent output chamber 582 and conduit 581. Multiple reservoirs may permit a user to mix a variety of substances in a single inhalation event, or to have multiple inhalation products available for delivery immediately.

In some embodiments, combined inhalant media may include any one of, or a combination of: suspension media (Vegetable Glycerin (VG) or Propylene Glycol (PG) or both), a drug, and a flavoring, a combination of drugs, or other combination of aerosols. In some embodiments, different drugs may be administered at different times during that day. For seniors, people who take multiple medications, or the cognitively impaired, this might be an ideal tool. The control circuit may be programmed via touch screen 528 (or a download or other) to sound alarm 526 to remind a user to inhale a given drug. Timer 527 may be set for this purpose. The control circuit may also monitor when a prescription has been taken (in case the user forgets).

In some embodiments, the device may communicate with the user or medical staff (configured as a "smart" device) to monitor whether a prescription has been taken, etc. In this and related manners, vaporizer device 410 may assist in controlling recreational or medical use of drugs or other additive media. In some embodiments, the electronic control circuit may record which aerosolization assemblies were activated, thereby enabling a user or healthcare provider to track the amount and frequency of use of drugs.

In some embodiments, the vaporizer device may limit the available dosage. In other embodiments, usage data, such as an overdose, may be communicated to a health monitoring system. For example, usage data may be communicated over a wireless network. In other examples, usage data may be communicated on the touch screen. In still other embodiments, usage data may be communicated through a physical download to a portable memory storage device, such as a flash drive.

Figures 3A, 3B:
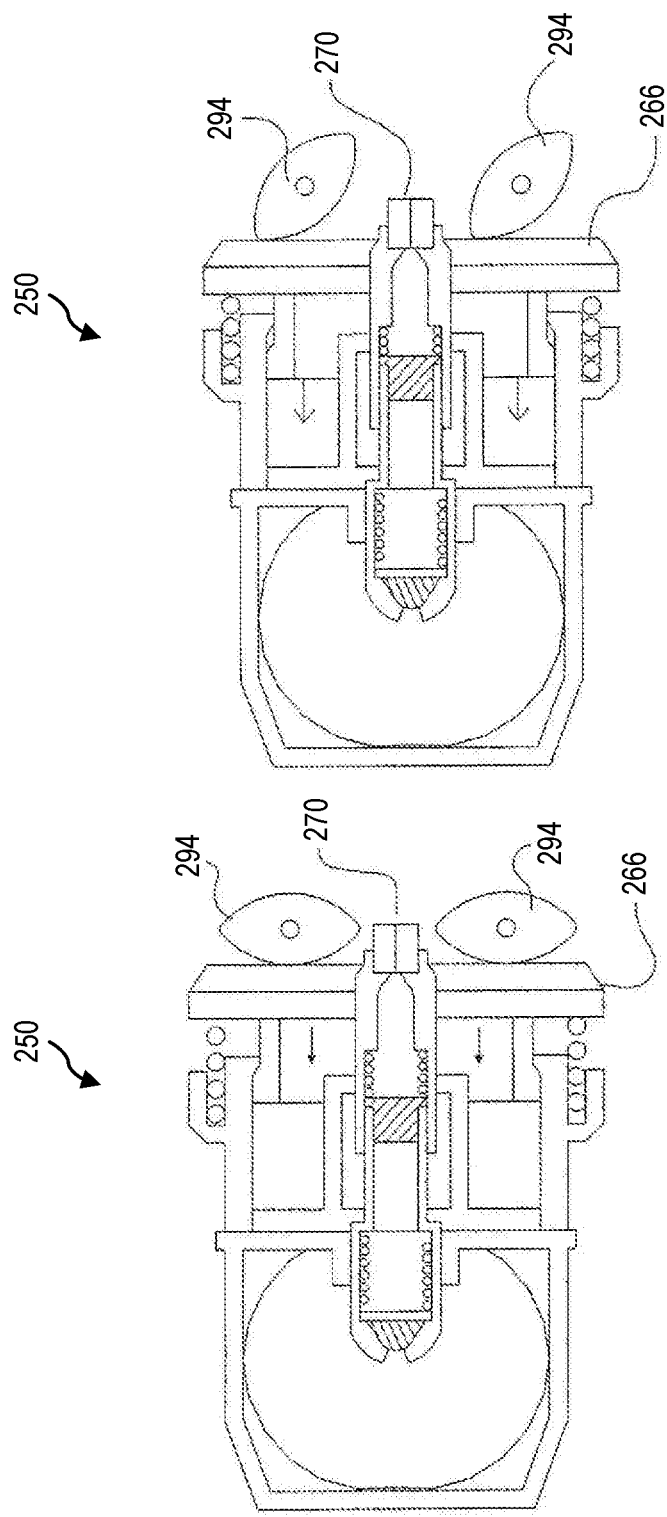
FIG. 3A and FIG. 3B are representations of a nebulizing assembly with an actuator, according to at least one embodiment of the present disclosure.
Figure 4:
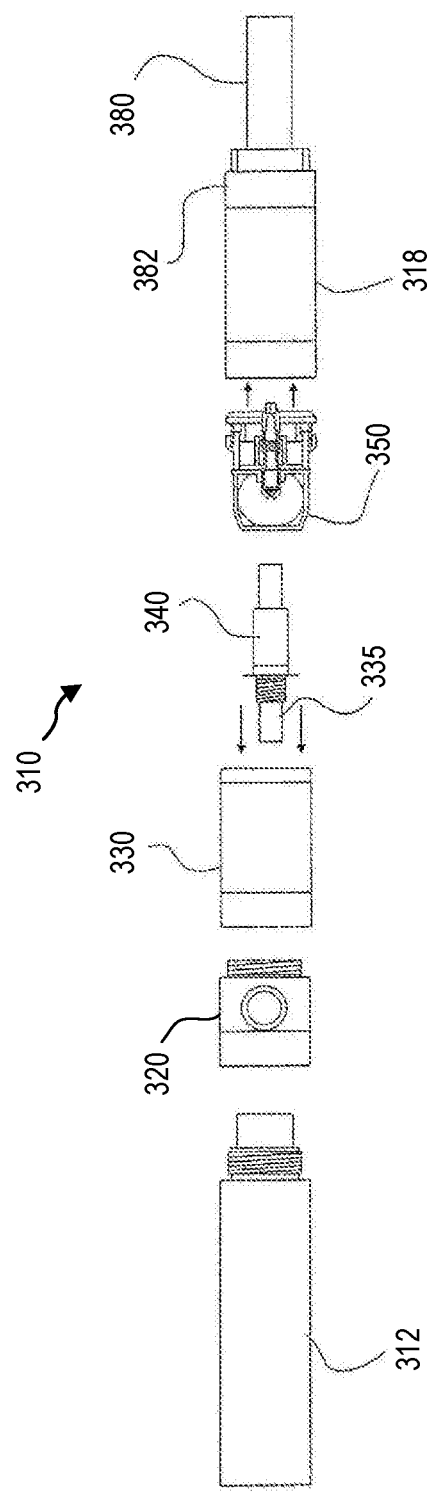
FIG. 4 is an exploded view of a vaporizer device including a thermal excitation assembly, according to at least one embodiment of the present disclosure.
Figure 5:
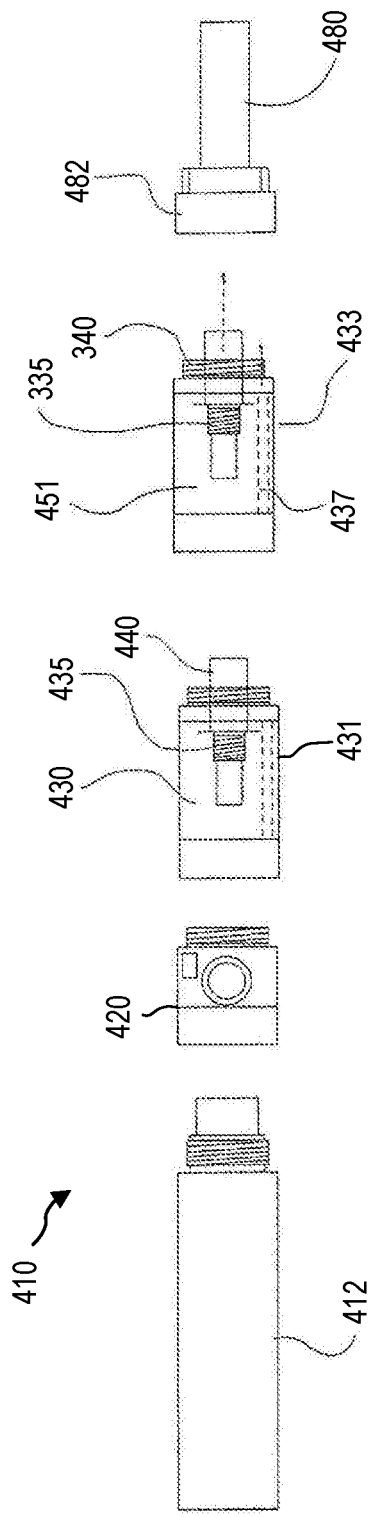
FIG. 5 is an exploded view of a vaporizer device including two cartridges including an inhalant media, according to at least one embodiment of the present disclosure.

In some embodiments, the vaporizer device may provide accurate dosing, adjustable dosing and/or multiple dosing. For example, if the volume of the piston chamber is known, and the concentration of the additive is also known, then the constriction of the piston chamber volume determines the delivered dose. Thus, one dose could be a complete depression of the piston, i.e., one volume of the piston chamber. Alternatively, if a smaller does is desired, the actuators discussed in reference to FIG. 3 may only be turned a predetermined amount, to partially depress the piston and deliver a reduced dose. Based on the size of the additive reservoir, multiple doses and/or multiple piston cycles may be executed from one additive media cartridge.

A device factor may be determined that represents the aerosolized product which condenses on the wall of the output chamber, conduit and/or mouthpiece walls. The device factor may be considered in dose determination. In addition, a user factor can be established based on research to determine the amount of inhalant product absorbed deep into the lungs and that absorbed by mouth and throat tissue, on average, for similar adjustment of initial dose.

Figure 7:
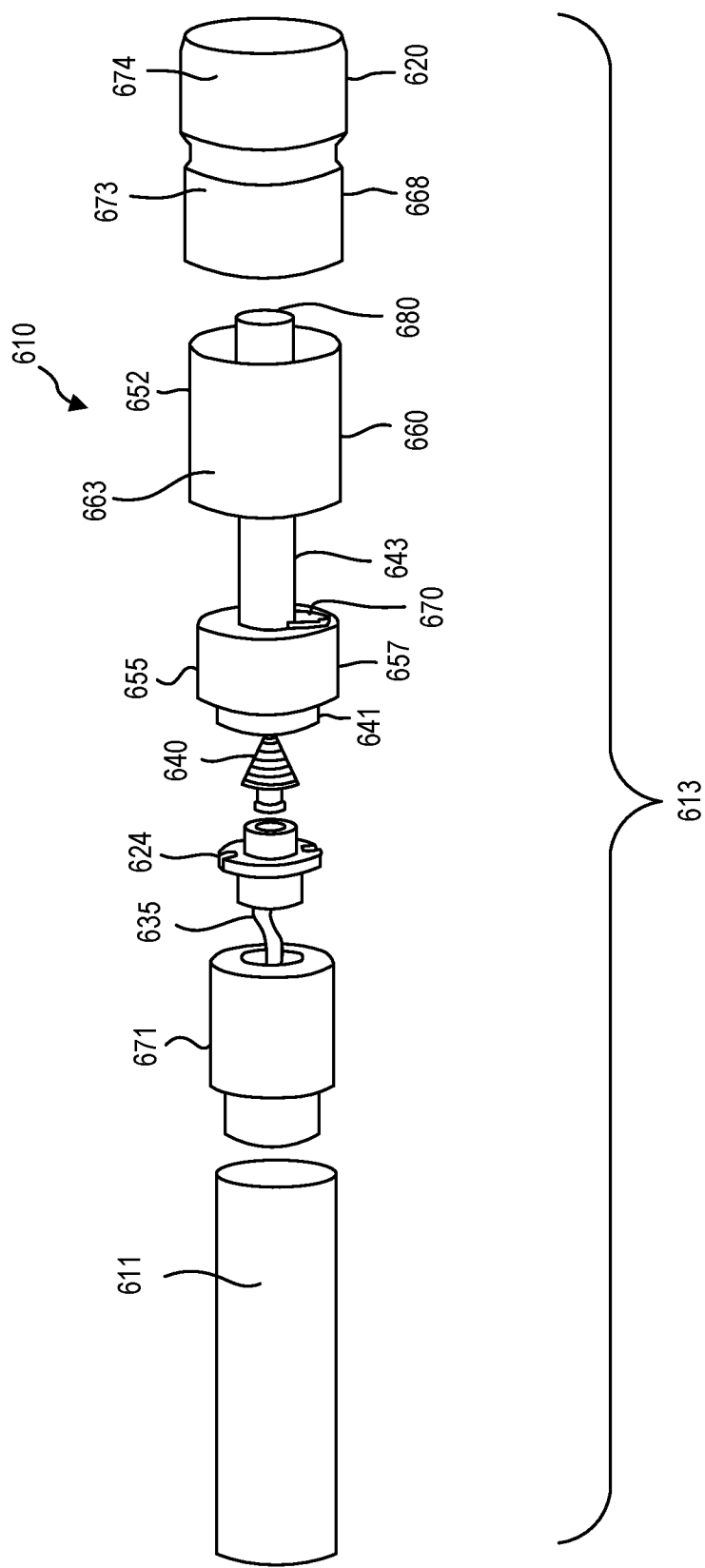
FIG. 7 is an exploded view of a vaporizer device according to at least one embodiment of the present disclosure.

Referring to FIG. 7, an exploded perspective view of at least one embodiment of an vaporizer 610 according to the present disclosure is shown.

Vaporizer device 610 may have a conventional e-cigarette base 613 that is combined with an additive media assembly 655 through which a fixed or set dose of a substance may be delivered to a user.

The conventional e-cigarette base 613 may include a battery 611 (rechargeable or not), a suspension reservoir 671, a wick 635, a coils support member 624, and a heating element 640. Conventional components of an EC may also include a heating chamber 641, the vaporizer body 643 and a mouthpiece 680. The suspension media may move through wicking wick 635 to heating element 640. Either due to inhalation by a user at mouthpiece 680 (a sensed event that can trigger coil activation) or a user pushing a control button or the like, the coil may be energized to heat the e-liquid to convert it from liquid to vapor.

In some embodiments, suspension media may include vegetable glycerin and propylene glycol-based products. In other embodiments, suspension media may include water. In some embodiments, the inhalant media may include flavoring, nicotine, and/or a controlled substance.

The additive media assembly 655 may include a coupling member 657, a nebulizer port 670, a piston 660 and piston cylinder, an inhalant media reservoir 652, a diaphragm 663, an actuator coupler 668, a control module 620, and control springs 673, 674.

The above components of the conventional base and additive assembly may be provided in a housing that may be more or less continuous or comprised of various inter-fitting segments. Suitable housing materials are known in the art.

In some embodiments, an additive media may be aerosolized in the heating chamber and made available for inhalation by a user. The additive media aerosol may mix with the suspension media aerosol in the heating chamber 641 or vaporizer body 643 before inhalation at the mouthpiece.

Figure 8:
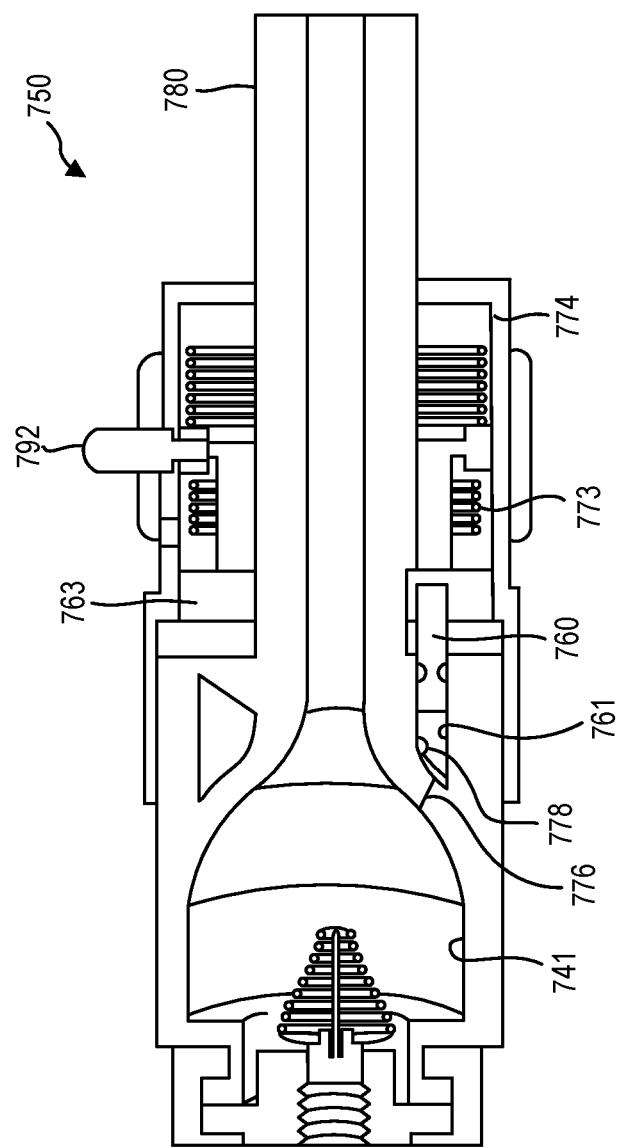
FIG. 8 is a nebulizer assembly according to at least one embodiment of the present disclosure.

Referring to FIG. 8, a cross-sectional view of at least one embodiment of a nebulizer assembly 750 is shown. In some embodiments, piston 760 may be disposed inside cylinder 761. Piston 760 may be coupled to diaphragm 763 which is controlled by the actuator 792 and springs 773 and 774. When piston 760 moves from a cocked configuration to an uncocked configuration, the inhalant media may be pulled into the evacuated cylinder. With a known cylinder volume and a known media concentration, a measured dose of target substance may enter the cylinder.

In a cocked configuration, expansion spring 774 may be configured to move the piston to the left. Rotation spring 773 may maintain actuator 792 in an off position. As the actuator rotates from the off position to an on position, the coil may energize for a thermal excitation event. When the coil reaches an excitation temperature, the actuator can finish rotation to the on position. This may cause spring 774 to push against the diaphragm and piston, moving piston 760 into cylinder 761 and evacuating the measured dose of the inhalant media.

In some embodiments, orifice 778 may be a fill orifice from which inhalant media may enter cylinder 761. A check valve may be provided at orifice 778 such that when piston 760 fills cylinder 761, the inhalant media in the cylinder may be forced out nebulizing opening 776. The nebulizing opening 776 may be configured to cause the additive media to enter heating chamber 741 as a mist. In some embodiments, the inhalant media may be substantially completely, uniformly and contemporaneously converted to an aerosol.

In some embodiments, when the inhalant media enters the heating chamber as a first aerosolized inhalant media, a second aerosolized inhalant media may already be in the heating chamber. In some embodiments, the second aerosolized inhalant media may include a suspension media, aerosolized from a suspension media reservoir. The first inhalant media and the second aerosolized inhalant media may mix in the heating chamber prior to inhalation at mouthpiece 780. In some embodiments, the first aerosolized inhalant media and the second aerosolized inhalant media mix in response to the Venturi effect, resulting from a reduction in ambient pressure that results when a substance flows through a constricted section (or choke) of a pipe.

Figure 9:
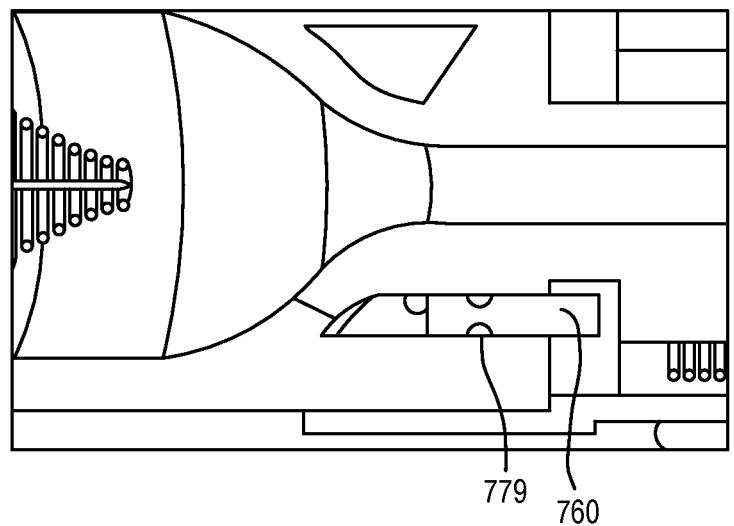
FIG. 9 is a representation of a nebulizer assembly piston in an uncocked configuration according to at least one embodiment of the present disclosure.
Figure 10:
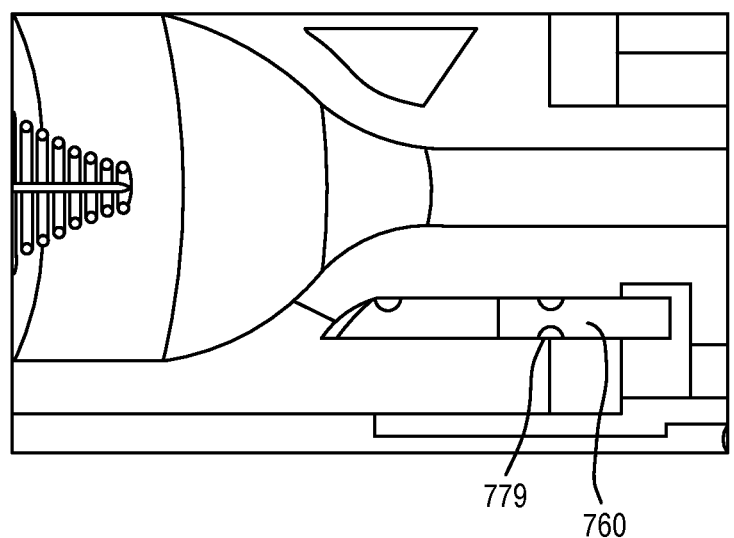
FIG. 10 is a representation of a nebulizer assembly piston in a cocked configuration according to at least one embodiment of the present disclosure.

Referring now to FIGS. 9 and 10, in some embodiments, the piston may cycle from an uncocked configuration to a cocked configuration. In some embodiments, the piston 760 may include a gasket 779 that may form an air- and liquid-tight seal, thereby preventing inadvertent release of additive media.

In some embodiments, devices described herein may be hybrid devices because they combine a suspension media and an additive media. In some embodiments, each inhalant media may be aerosolized independently. For example, in a vaporizer device including a suspension media and an additive media, the suspension media may be aerosolized independent of the additive media. In other examples, the additive media may be aerosolized independently of the suspension media. In other embodiments, each inhalant media in a vaporizer device may be aerosolized in one event. In still other embodiments, any combination of inhalant media may be aerosolized in one event. For example, in a vaporizer device having three inhalant media, two of the three inhalant media may be aerosolized in one event. In other examples, in a vaporizer device having five inhalant media, three may be aerosolized in one event.

In some embodiments, in a vaporizer device including suspension media and additive media, both the suspension media and additive media may be aerosolized using the same method. For example, both the suspension media and the additive media may be aerosolized using thermal excitation. In other examples, both the suspension media and the additive media may be aerosolized using a nebulizing assembly. In other embodiments, the suspension media and the additive media may be aerosolized using different methods. For example, the suspension media may be aerosolized using thermal excitation and the additive media may be aerosolized using a nebulizing assembly. In other examples, the suspension media may be aerosolized using a nebulizing assembly and the additive media may be aerosolized using thermal excitation.

In some embodiments, the thermal excitation of an inhalant media may moisten and prepare the airway for additional inhalants. For example, a suspension media may prepare the airway when inhaled after aerosolization by thermal excitation. After the airway is prepared, an additive media, alone or in combination with a suspension media, may be effectively carried into the lungs. In some embodiments, thermal excitation of an inhalant media may and clean or evacuate both the device and mouth and throat after the nebulizer dosing event. In some embodiments, this may enable delivery of an accurate dose to the proper location, even at low doses.

In some embodiments, a dosing event or dosing cycle may begin with thermal excitation of a suspension media for a first period of time, the first period of time being prior to the additive media aerosolization. In some embodiments, thermal excitation may continue through a second period of time, the second period of time being during the additive media aerosolization. In some embodiments, thermal excitation may continue through a third period of time, the third period of time being after the additive media aerosolization. In some embodiments, thermal excitation of the suspension media during the first period of time prepares, or primes, the airway for the additive media, which may encourage more complete uptake of the additive media product. Continuing thermal excitation of the suspension media for the third period of time may help ensure transfer of the additive media to the user.

In some embodiments, the orientation of the nebulizer assembly relative to the vaporizer may be altered to suit the substances that are being inhaled. For example, if the nebulized substance is not flammable, the nebulized inhalant media may be dispensed directly at a heating element. In other examples, a flammable nebulized substance may ignite upon contact with a heating element. Directing the nebulizer assembly such that the nebulized substance is dispensed away from the heating element may reduce the likelihood of ignition.

Figure 11:
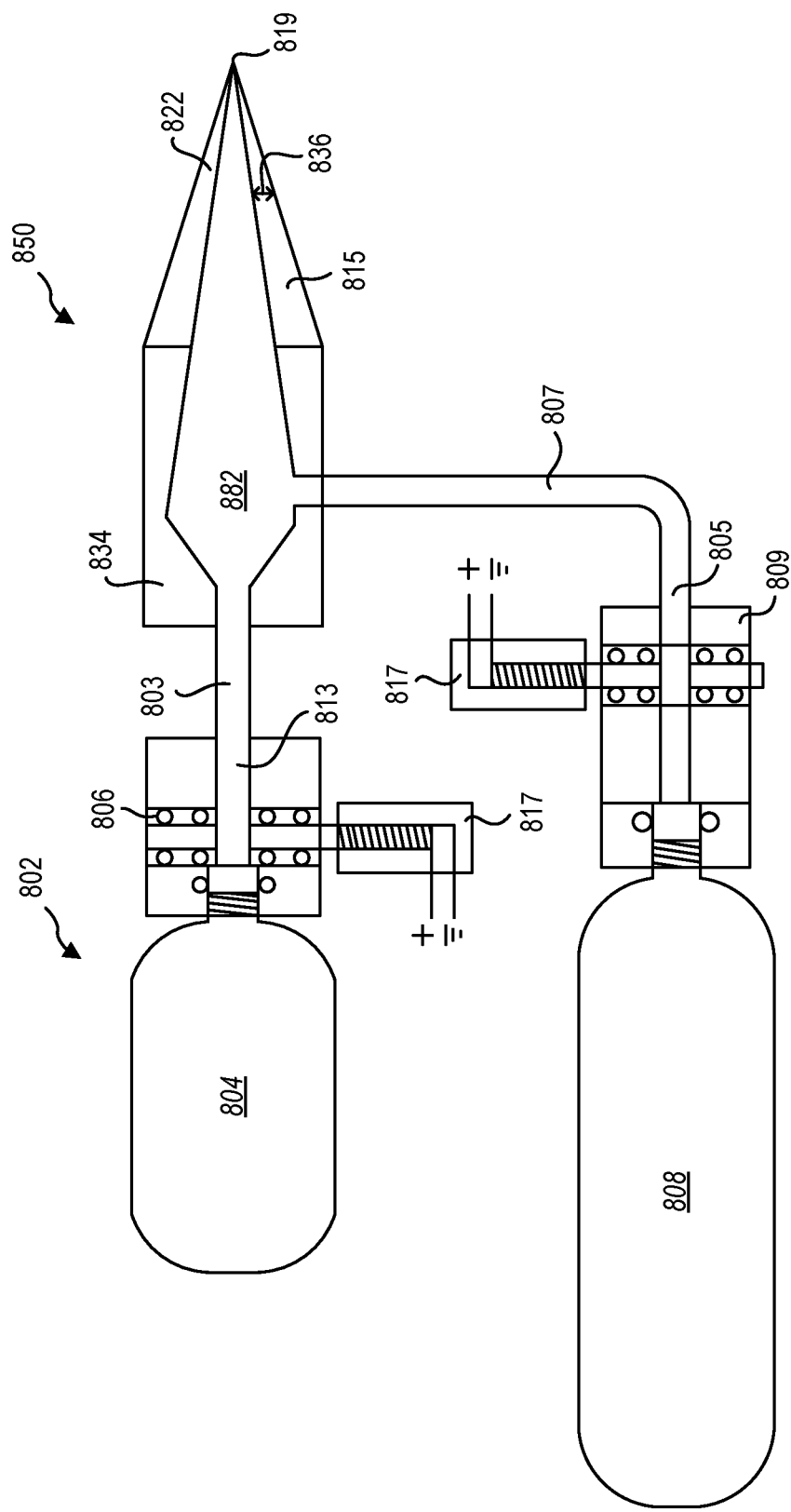
FIG. 11 is a representation of a nebulizer assembly utilizing a plurality of pressurized cartridges and a nozzle, according to at least one embodiment of the present disclosure.

Referring now to FIG. 11, the nebulizer assembly 850 may include one or more cartridges of a pressurized inhalant media. For example, an additive assembly 802 may include an additive pressurized cartridge 804 filled with an additive media and connected to an additive solenoid valve 806. In some embodiments, The additive pressurized cartridge 804 may utilize an additive pressure of up to 900 psi. In some embodiments, the additive pressure may be within a range including a lower limit, an upper limit, or both lower and upper limits including any of 500 psi, 550 psi, 600 psi, 650 psi, 700 psi, 750 psi, 800 psi, 850 psi, 900 psi, 950 psi, 1000 psi, or values therebetween. For example, the additive pressure may be greater than 500 psi. In other examples, the additive pressure may be less than 1000 psi. In still other examples the additive pressure may be any value in a range between 500 psi and 1000 psi. In some embodiments, it may be critical to operation that the additive pressure be between 500 psi and 1000 psi.

The nebulizer assembly 850 may also include a suspension pressurized cartridge 808 filled with a suspension media. The suspension pressurized cartridge 808 may be connected to a suspension solenoid valve 809. The suspension pressurized cartridge 804 may utilize a suspension pressure of up to 900 psi. In some embodiments, the suspension pressure may be within a range including a lower limit, an upper limit, or both lower and upper limits including any of 500 psi, 550 psi, 600 psi, 650 psi, 700 psi, 750 psi, 800 psi, 850 psi, 900 psi, 950 psi, 1000 psi, or values therebetween. For example, the suspension pressure may be greater than 500 psi. In other examples, the suspension pressure may be less than 1000 psi. In still other examples the suspension pressure may be any value in a range between 500 psi and 1000 psi. In some embodiments, it may be critical to operation that the suspension pressure is between 500 psi and 1000 psi.

The additive solenoid valve 806 may be a shuttle valve. In some embodiments, the shuttle valve may house o-ring seals. In other embodiments, the shuttle valve may have an integral o-ring. The additive solenoid valve 806 may have a cross drilled orifice 813 that opens into an additive pathway 803. The additive pathway 803 opens into mixing chamber 882.

Similarly, the suspension solenoid valve 809 may be a shuttle valve. In some embodiments, the shuttle valve may house o-ring seals. In other embodiments, the shuttle valves have o-rings themselves. The suspension solenoid valve 809 may have a cross drilled orifice 805 that opens into a suspension pathway 807. The suspension pathway 807 opens into the mixing chamber 882.

In some embodiments, the additive solenoid valve 806 and the suspension solenoid valve 809 may be powered using a power source 817. In some embodiments, the additive solenoid valve 806 may have a different power source 817 than the suspension solenoid valve 809. In other embodiments, the additive solenoid valve 806 and the suspension solenoid valve 809 may have the same power source 817. The power source 817 may be a battery. In some embodiments, the battery may be a disposable or replaceable battery (e.g., a single-use battery, or a non-rechargeable battery). In other embodiments, the battery may be rechargeable. For example, the battery may be recharged using a standard 110 volt wall plug-in charger, such as a micro-USB charger. In other examples, the battery may be recharged using solar panels mounted to the nebulizer assembly.

In some embodiments, the additive solenoid valve 806 and the suspension solenoid valve 809 may include a timer. The timer may be configured to maintain an open position of the additive solenoid valve 806 and/or the suspension solenoid valve 809 for a predetermined dosing period. The combination of the dosing period and a flow rate through the nozzle 815 may determine a dose of additive or suspension media to be released. In some embodiments, the dosing period for the additive and the suspension media may be the same. In other embodiments, the dosing period of the additive and the suspension media may be different.

In some embodiments, the suspension media may be released (e.g., the suspension solenoid valve 809 may be open) before, during, and after the additive is released (e.g., the additive solenoid valve 806 is open). In other embodiments, the suspension media may be released before and during the additive is released. In still other embodiments, the suspension media may be released during and after the additive is released. In yet other embodiments, the suspension media may be released before and after the additive is released, but not during release of the additive. In further embodiments, the suspension media may be released for one of before, during, or after the additive is released.

In some embodiments, the additive pressurized cartridge 804 may be connected to the additive solenoid valve 806 using a threaded connection. In other embodiments, the additive pressurized cartridge 804 may be connected to the additive solenoid valve 806 using a snap connection. In still other embodiments, the additive pressurized cartridge 804 may be connected to the additive solenoid valve 806 using any type of connection as known in the art.

In some embodiments, the suspension pressurized cartridge 808 may be connected to the suspension solenoid valve 809 using a threaded connection. In other embodiments, the suspension pressurized cartridge 808 may be connected to the suspension solenoid valve 809 using a snap connection. In still other embodiments, the suspension pressurized cartridge 808 may be connected to the suspension solenoid valve 809 using any type of connection as known in the art.

The mixing chamber 882 includes a nozzle 815 at a distal end, or an end opposite the entry of the additive pathway 803 and the suspension pathway 807. The nozzle 815 includes a small distal orifice or nozzle opening 819 of the mixing chamber. The nozzle opening 819 may be 5 micrometers. In some embodiments, the nozzle opening 819 may be within a range including a lower limit, an upper limit, or both lower and upper limits including any of 1 micrometer, 2 micrometers, 3 micrometers, 4 micrometers, 5 micrometers, 6 micrometers, micrometers, 8 micrometers, 9 micrometers, 10 micrometers, 11 micrometers, 12 micrometers, 13 micrometers, 14 micrometers, 15 micrometers, 16 micrometers, 17 micrometers, 18 micrometers, 19 micrometers, 20 micrometers, or values therebetween. For example, the nozzle opening 819 may be greater than 1 micrometer. In other examples, the nozzle opening 819 may be less than 20 micrometers. In still other examples the nozzle opening 819 may be any value in a range between 1 micrometers and 20 micrometers. In some embodiments, it may be critical to operation that the nozzle opening 819 be less than 20 micrometers.

As the additive and suspension media move through the nozzle 815, nanoliter scale droplets are ejected out the nozzle. These droplets are small enough to pass beyond the carina into the lungs where they can be reliably absorbed into the bloodstream.

The relative importance of the size of the nozzle opening 819 can be observed with the location of the variable A2 in the Venturi flow equation shown below:

$$Q = A_2 \sqrt{\frac{2(p_1 - p_2)}{\rho\left(1 - \left(\frac{A_2}{A_1}\right)\right)^2}}$$

where Q is the volumetric flow rate, $p_1$ and $p_2$ are the inside and outside pressure, respectively; $\rho$ is the air density, and $A_1$ and $A_2$ are the mixing chamber area and nozzle opening 819 area, respectively. Thus, it can be seen that as $A_2/A_1$ increases, the flow rate of the gas and fluid mixture ejected out of the nozzle also decreases proportionally.

For example, for a mixing chamber with a profile that changes from 75 square millimeters to 0.0003 square millimeters (e.g., a 20 micrometer nozzle opening 819) and from 900 psi to 1 psi, the flow rate of a gas mixture with a density of 1.38 kg/cubic meters through the orifice is 0.3 cubic millimeters per second (or 0.06 liters per minute).

Lung inhalation rates may be between 0.1-0.2 liters/min. Therefore, utilizing a nozzle opening 819 of less than 20 micrometers may deliver nanoliter scale particles at a relatively steady flow into the alveolus.

The nozzle opening 819 is bounded by a nozzle wall 822. In some embodiments, the nozzle wall 822 has a nozzle wall thickness 836 that may decrease in thickness from the proximal end 834 of the nozzle 815 to the nozzle opening 819. In some embodiments, the nozzle wall thickness 836 at the nozzle opening 819 may be less than 200 micrometers. In some embodiments, the nozzle wall thickness 836 may be within a range including a lower limit, an upper limit, or both lower and upper limits including any of 150 micrometers, 160 micrometers, 170 micrometers, 180 micrometers, 190 micrometers, 200 micrometers, 210 micrometers, 220 micrometers, 230 micrometers, 240 micrometers, 250 micrometers, or values therebetween. For example, the nozzle wall thickness 836 may be greater than 150 micrometers. In other examples, the nozzle wall thickness 836 may be less than 250 micrometers. In still other examples the nozzle wall thickness 836 may be any value in a range between 150 micrometers and 250 micrometers. The pressure inside the mixing chamber 882 may not compromise the nozzle wall 822 because of the lowered pressures sustained through the Venturi effect.

In some embodiments, the suspension pressure and the additive pressure may be the same. In other embodiments, the suspension pressure and the additive pressure may be different. In some embodiments, the nebulizer assembly 850 may be configured with a single additive pressurized cartridge 804 and no suspension pressurized cartridge. The suspension media may be nebulized using any of the devices and methods discussed above. For example, the suspension media may be nebulized using the displacement nebulizing assembly of FIG. 3A and FIG. 3B. In other examples, the suspension media may be nebulized using a thermal excitation assembly.

Figure 12:
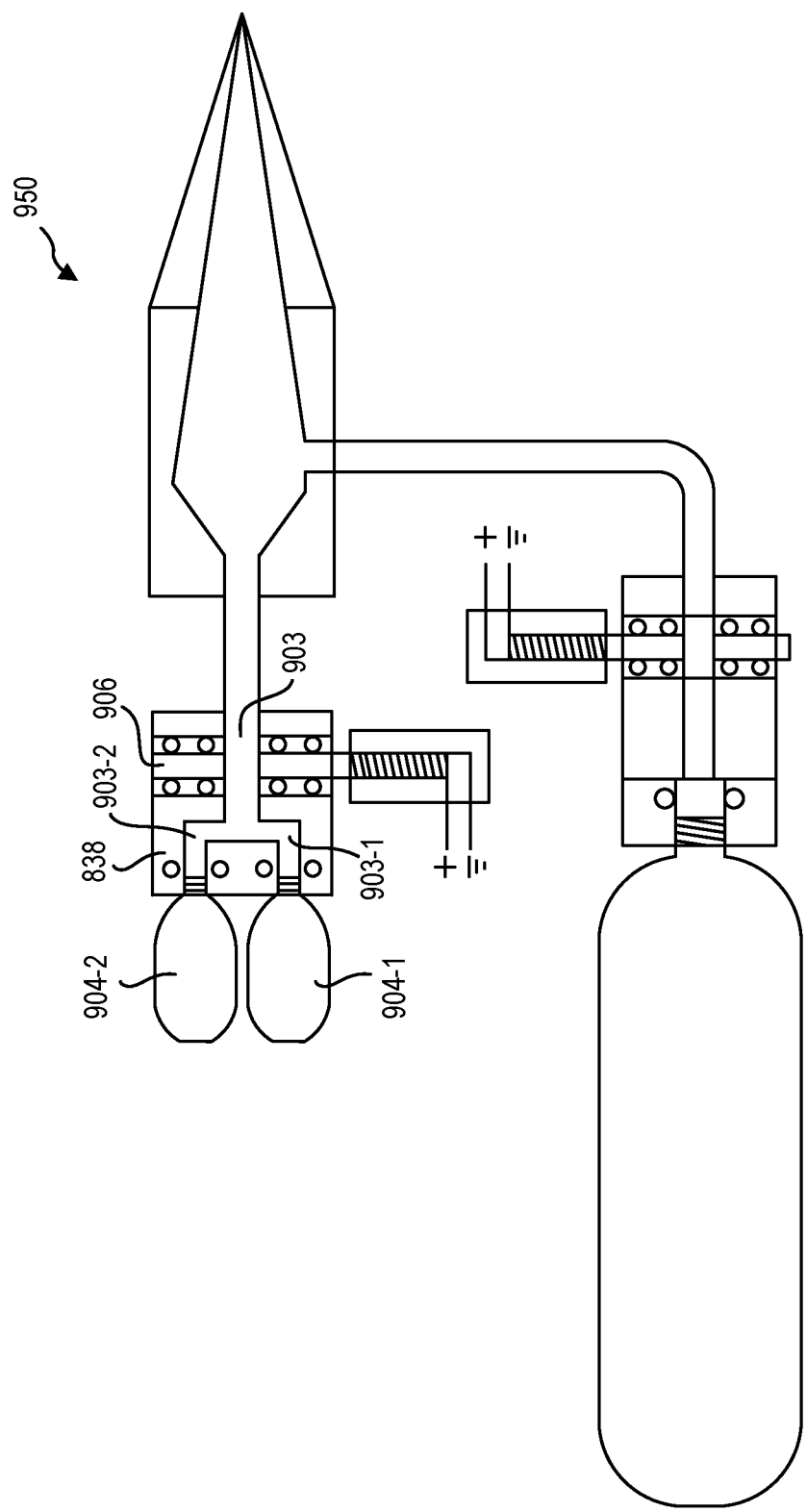
FIG. 12 is another representation of a nebulizer assembly utilizing a plurality of pressurized cartridges and a nozzle, according to at least one embodiment of the present disclosure.

FIG. 12 is a representation of a nebulizer assembly 950 that may include all or some of the features described above, particularly in relation to FIG. 11. In some embodiments, the nebulizer assembly 950 may include more than one additive pressurized cartridge 904-1, 904-2. For example, the nebulizer assembly 950 may include two additive pressurized cartridges 904-1, 904-2. In other examples, the nebulizer assembly 950 may include three, four, five, or six pressurized cartridges 904-1, 904-2.

In some embodiments, each of the additive pressurized cartridges 904-1, 904-2 may include the same additive. In other embodiments, each of the additive pressurized cartridges 904-1, 904-2 may include different additives.

Each of the additive pressurized cartridges 904-1, 904-2 may be connected to an additive manifold 838. Each additive pressurized cartridge 904-1, 904-2 may open into an additive pathway 903-1, 903-2. In some embodiments, the additive pathways 903-1, 903-2 may combine into a combined additive pathway 903. An additive solenoid valve 906 may be located in the combined additive pathway 903 downstream of the additive pathways 903-1, 903-2. In this manner, actuation of the additive solenoid valve 906 may release additive from both additive pressurized cartridges 904-1, 904-2 simultaneously.

Figure 13:
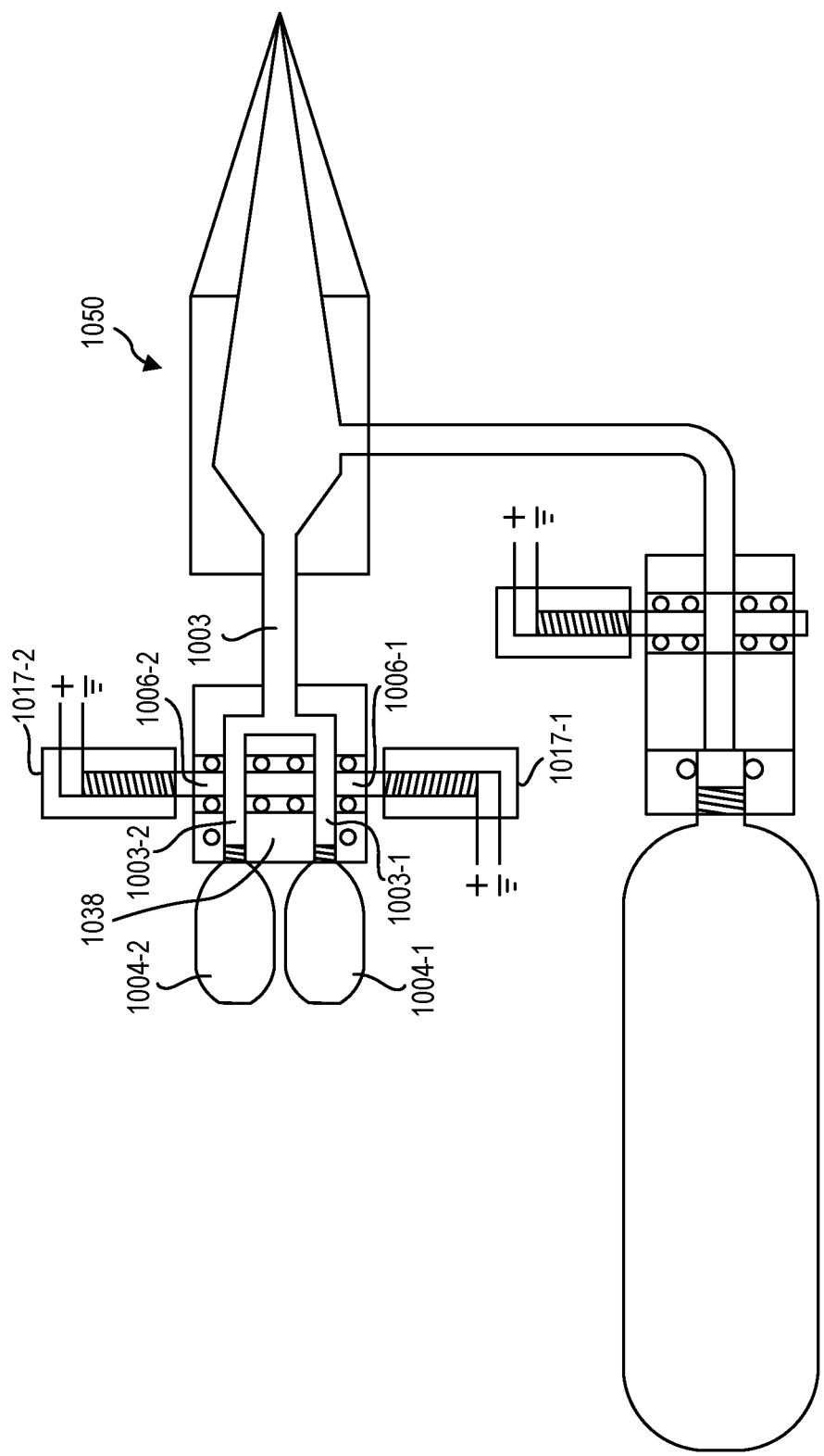
FIG. 13 is another representation of a nebulizer assembly utilizing a plurality of pressurized cartridges and a nozzle, according to at least one embodiment of the present disclosure.

FIG. 13 is a representation of a nebulizer assembly 1050 that may include all or some of the features described above, particularly in relation to FIGS. 11 and 12. In some embodiments, the nebulizer assembly 1050 may include a plurality of additive pressurized cartridges 1004-1, 1004-2 may be connected to an additive manifold 1038. Each pressurized cartridge 1004-1, 1004-2 may open into an additive pathway 1003-1, 1003-2. The additive pathways 1003-1, 1003-2 may combine into a combined additive pathway 1003.

In some embodiments, an additive solenoid valve 1006-1, 1006-2 may be located at each additive pathway 1003-1, 1003-2. In some embodiments, each additive solenoid valve 1006-1, 1006-2 may have its own power source 1017-1, 1017-2. Thus, each additive solenoid valve 1006-1, 1006-2 may be actuated independently. In this manner, different additives or inhalant media may be selectively actuated, depending on the preferences of a user or a treatment regimen prescribed by a doctor. In other embodiments, each two or more additive solenoid valves 1006-1, 1006-2 may be actuated simultaneously if simultaneous delivery of two or more additives is desired or prescribed.

Figure 14:
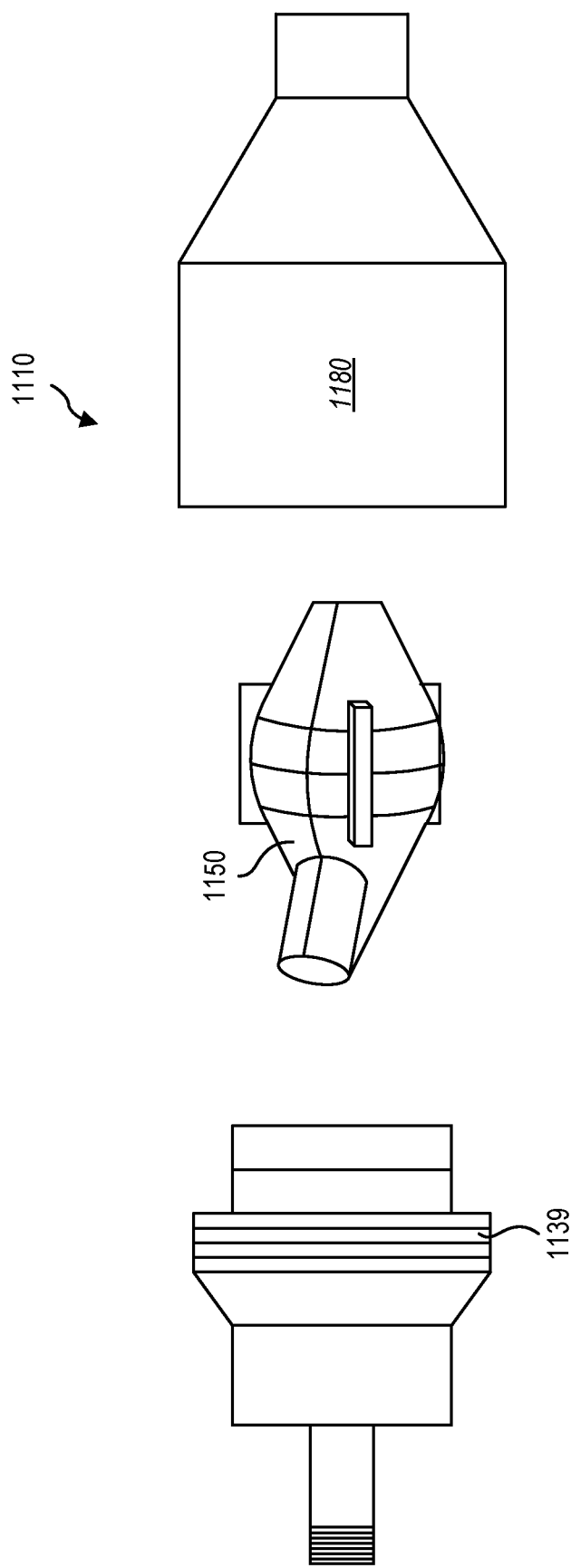
FIG. 14 is a representation of an e-cigarette housing, according to at least one embodiment of the present disclosure.

FIG. 14 is a representation of a vaporizer device 1110 that may include all or some of the features described above, particularly in relation to FIGS. 11, 12, and 13. In some embodiments, the vaporizer device 1110 may include a plurality of interconnecting housing sections. Each of the interconnecting housing sections may include a different portion of the vaporizer device 1110. For example, one interconnecting housing section may include a nebulizer assembly 1150. Another interconnecting housing section may include a nebulizer housing 1139. Another interconnecting housing section may include a mouthpiece 1180. Still further interconnecting housing sections may including decorations, handles, spare batteries, and other housing sections.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A vaporizer device, comprising:
   a plurality of pressurized cartridges, wherein at least two pressurized cartridges of the plurality of pressurized cartridges include a pressurized inhalant media; and
   a solenoid valve in communication with the plurality of pressurized cartridges; and
   at least one nebulizing assembly configured to nebulize the inhalant media, the at least one nebulizing assembly consisting of:
      a mixing chamber configured to receive pressurized inhalant media from the at least two pressurized cartridges based on an opening of the solenoid valve;
      a nozzle with a nozzle opening that is less than 20 micrometers, wherein the nozzle opening is configured to deliver nanoliter scale particles of the pressurized inhalant media based on the venturi effect; and
      a nozzle wall that decreases in wall thickness from a proximal end of the nozzle to the nozzle opening.

2. The vaporizer device of claim 1, wherein the at least two pressurized cartridges include at least one of a suspension media and an additive media.

3. The vaporizer device of claim 2, wherein the suspension media includes at least one of vegetable glycerin and propylene glycol.

4. The vaporizer device of claim 2, wherein the additive media includes at least one of a drug and a flavoring.

5. The vaporizer device of claim 1, wherein at least one pressurized cartridge of the plurality of pressurized cartridges includes a nebulizing assembly or a thermal excitation assembly.

6. The vaporizer device of claim 1, wherein the pressurized inhalant media is pressurized to a pressure of 900 psi.

7. The vaporizer device of claim 1, wherein at least one of the plurality of pressurized cartridges includes a suspension media and at least one of the plurality of pressurized cartridges includes an additive media.

8. The vaporizer device of claim 1, wherein the solenoid valve is a shuttle valve.

9. The vaporizer device of claim 8, wherein the solenoid valve includes a timer configured to open the solenoid valve for a dosing period to provide a measured dose.

10. A vaporizer device, comprising:
a plurality of pressurized inhalant media reservoirs, each pressurized inhalant media reservoir including an inhalant media;
a plurality of solenoid valves, each solenoid valve of the plurality of solenoid valves being associated with a pressurized inhalant media reservoir of the plurality of pressurized inhalant media reservoirs;
a plurality of nebulizing assemblies connected to the plurality of pressurized inhalant media reservoirs, wherein the plurality of nebulizing assemblies are configured to nebulize the inhalant media using the venturi effect through a restricted nozzle opening to deliver nanoliter scale particles of the inhalant media; and
an electronic control circuit in electrically coupled with the plurality of nebulizing assemblies.

11. The vaporizer device of claim 10, each pressurized inhalant media reservoir of the plurality of pressurized inhalant media reservoirs including different inhalant media, and wherein the different inhalant media include at least one of a suspension media and an additive media.

12. The vaporizer device of claim 11, wherein the plurality of nebulizing assemblies are locked, and wherein the electronic control circuit is configured to unlock at least one nebulizing assembly of the plurality of nebulizing assemblies according to instructions from a user.

13. The vaporizer device of claim 11, wherein the electronic control circuit records which nebulizing assemblies of the plurality of nebulizing assemblies are activated.

14. The vaporizer device of claim 11, wherein the electronic control circuit communicates usage data to a user.

15. A method for vaporizing an inhalant, comprising:
opening a suspension solenoid valve of a vaporizer device, the vaporizer device including a pressurized suspension cartridge connected to a mixing chamber by a suspension pathway, wherein the suspension solenoid valve is located on the suspension pathway, the vaporizer device further including a pressurized additive cartridge connected to the mixing chamber by an additive pathway, wherein an additive solenoid valve is located on the additive pathway;
releasing a pressurized suspension media from the pressurized suspension cartridge into the mixing chamber through the suspension pathway when the suspension solenoid valve is opened;
after at least a portion of the pressurized suspension media enters the mixing chamber, opening the additive solenoid valve for a dosing period;
releasing a pressurized additive media from the pressurized additive cartridge into the mixing chamber through the additive pathway when the additive solenoid valve is opened;
mixing the pressurized suspension media and the pressurized additive media in the mixing chamber; and
nebulizing the mixed pressurized suspension media and pressurized additive media by moving through a nebulizing assembly having a nozzle opening of less than 20 micrometers, wherein the mixed pressurized suspension media and pressurized additive media are nebulized into nanoliter scale droplets based on a pressure of the pressurized suspension media and the pressurized additive media, an area of the mixing chamber, and an area of the nozzle opening.

16. The method of claim 15, wherein opening the additive solenoid valve for the dosing period includes measuring a measured dose using a timer.

17. The method of claim 16, further comprising mixing the measured dose with a the pressurized suspension media by opening the suspension solenoid valve before, during, and following opening the additive solenoid valve.

18. The method of claim 15, further comprising actuating the nebulizing assembly using an actuator in electronic communication with an electronic control circuit.

19. The method of claim 15, wherein at least one of the pressurized suspension cartridge or the pressurized additive cartridge includes the nebulizing assembly.

20. The method of claim 15, wherein the mixed pressurized suspension media and pressurized additive media are nebulized into nanoliter scale droplets based on the venturi effect.

* * * * *